(12) United States Patent
Larsen et al.

(10) Patent No.: US 8,168,229 B2
(45) Date of Patent: May 1, 2012

(54) METHODS FOR MAKING A MULTICOMPONENT HEMOSTATIC DRESSING

(75) Inventors: Gustavo Larsen, Lincoln, NE (US); Ruben Spretz, Lincoln, NE (US)

(73) Assignee: LNK Chemsolutions, LLC, Lincoln, NE (US)

( * ) Notice: Subject to any disclaimer, the term of this patent is extended or adjusted under 35 U.S.C. 154(b) by 668 days.

(21) Appl. No.: 12/299,842

(22) PCT Filed: Sep. 27, 2006

(86) PCT No.: PCT/IB2006/053526
§ 371 (c)(1),
(2), (4) Date: Nov. 6, 2008

(87) PCT Pub. No.: WO2007/135492
PCT Pub. Date: Nov. 29, 2007

(65) Prior Publication Data
US 2009/0181072 A1 Jul. 16, 2009

Related U.S. Application Data

(60) Provisional application No. 60/747,614, filed on May 18, 2006.

(51) Int. Cl.
*A61K 35/16* (2006.01)
*A61F 13/00* (2006.01)

(52) U.S. Cl. .......................................... 424/530; 602/41

(58) Field of Classification Search ........................ None
See application file for complete search history.

(56) References Cited

U.S. PATENT DOCUMENTS

| | | | | |
|---|---|---|---|---|
| 6,056,970 | A * | 5/2000 | Greenawalt et al. | 424/426 |
| 6,762,336 | B1 * | 7/2004 | MacPhee et al. | 602/48 |
| 2002/0156498 | A1 * | 10/2002 | Jo et al. | 606/213 |

OTHER PUBLICATIONS

Rtohwell S.W. et al. Thrombosis Research 108 (2003) 335-340.*
Li Z. et al. Journal of Applied Polymer Science, vol. 84 (2002) pp. 2049-2059.*
Tamura H. et al. Carbohydrate Polymers, vol. 56 (2004) pp. 205-211.*

* cited by examiner

*Primary Examiner* — Stephen Kapushoc
(74) *Attorney, Agent, or Firm* — Louis Ventre, Jr.

(57) ABSTRACT

A method of making a pliable, bioabsorbable hemostatic dressing wherein the dressing is composed of fibers with at least one molecular-scale coating, which upon first contact with blood and due to a large area of contact with blood per unit weight of active ingredients, initiates and accelerates the biochemical blood clotting cascade processes. The steps of the method include dissolving in an organic solvent one or more soluble bioabsorbable polymers and organic or aqueous-organic media of non-protein constituents to create a homogeneous mixture; forming fibers from the homogeneous mixture; adding to the fibers a molecular-scale first coating of one or more proteins of blood clotting species that minimally react with each other; and optionally adding a second coating of one or more proteins of blood clotting species to the fibers that minimally react with each other and that, together with the one or more proteins of blood clotting species in the molecular-scale first coating, induce blood coagulation in the presence of blood. The fibers may optionally have occluded in them or at their surface other chemicals of abiological or biological origin that aid in the blood clotting process.

1 Claim, 2 Drawing Sheets

11 — dissolving in an organic solvent one or more soluble bioabsorbable polymers and organic or aqueous-organic media of non-protein constituents to create a homogeneous mixture

12 — forming fibers from the homogenous mixture

13 — adding to the fibers a molecular-scale first coating of one or more proteins of blood clotting species that minimally react with each other

FIG.1

20 — dissolving in an organic solvent one or more soluble bioabsorbable polymers, one or more proteins of blood clotting species that minimally react with each other, and organic or aqueous-organic media of non-protein constituents to create a homogeneous mixture

12 — forming fibers from the homogeneous mixture

21 — adding to the fibers a coating of one or more proteins of blood clotting species that minimally react with each other and that, together with the one or more proteins of blood clotting species in the fibers, induce blood coagulation in the presence of blood

FIG.2

METHODS FOR MAKING A MULTICOMPONENT HEMOSTATIC DRESSING

CROSS-REFERENCE TO RELATED APPLICATIONS

The present invention claims the benefit of the filing date of prior U.S. provisional application 60/747,614 filed 18 May 2006, the text of which is included by reference herein.

GOVERNMENT LICENSE RIGHTS

The U.S. Government has a paid-up license in this invention and the right in limited circumstances to require the patent owner to license others on reasonable terms as provided for by the terms of contract No. 2004-02653 awarded by the United States Department of Agriculture and contract No. 1 R43 ES013367-01 A1 awarded by the National Institutes of Health.

TECHNICAL FIELD

This invention relates to hemostatic compositions useful in the stemming or prevention of blood loss from battlefield injuries, surgical procedures and traumatic wounds.

BACKGROUND ART

During the 1980's and early 1990's, increased awareness of the HIV and hepatitis propagation potential resulting from use of unpurified blood and blood products hampered the development of safe and effective human fibrinogen-based hemostatic dressings. However, subsequent developments on recombinant fibrinogen and recombinant blood factors, as well as on improvements in plasma purification methods, started reversing that trend.

The preferred embodiment of the present invention includes fibrinogen and/or other blood clotting species in a molecular-scale coating on individual fibers of the dressing. The term "molecular-scale coating" refers to a coating with a thickness equivalent from one to about several molecular layers. A typical molecule in blood clotting species is human fibrinogen, which is a protein with a molecular weight of approximately 341,000, and with an oblong shape and a characteristic maximum length of approximately 47 nanometers.

Prior art inclusion of fibrinogen or other blood clotting species in a dressing are typically in multilayered a structure of a distinct layer of blood clotting species, which is, generally evident to the naked eye, and not in a molecular-scale coating which cannot be discerned with the naked eye. The surface of each such distinct layer exposes the blood clotting species to blood and surrounding air. Each such distinct layer has a characteristic length, such as thickness and grain size, that is larger than the average fiber diameter and the thickness of the coating of blood clotting species on any fibers in the present invention. Coatings referred to in the prior art refer to a distinctly different layered coating on the dressing. Unlike the present invention, a prior art coating of active components does not refer to a well mixed coating on the bulk of the fibers in the dressing. Prior art layers are distinctly different and much less efficient than a molecular-scale coating on individual fibers enabled by the method of the present invention.

U.S. Pat. No. 6,056,970 to K. E. Greenawalt, et al. is an improvement over layered dressings. Greenawalt teaches a fibrous dressing wherein the coagulation protein is dispersed throughout the hemostatic composition, but not in a molecular-scale coating on the bulk of the fibers in the dressing. Rather Greenawalt discloses dispersal within the fibers in a manner that captures comparatively larger domains of the protein within the fiber structure. Greenawalt also teaches compressing the fibers into a paper-like compositions so as to prevent activation of fibrinogen during processing. The present invention is an improvement in that the protein is captured in a fiber or as a molecular-scale coating on individual fibers, such that it significantly increases the surface area of exposure of coagulation protein to the blood.

Methods of electrospinning fibers for dressings that contain coagulation proteins are well known. For example, United States Patent Application Publication No. 20060013863 A1 to S. W. Shalaby, et al. published on Jan. 19, 2006 describes such methods and the formation of hemostatic, compliant, elastomeric, multicomponent, fibrous dressings. This prior art, however, but does not teach molecular-scale coatings on the fibers such that a coagulum is formed when exposed to blood.

There are a number of synthetic agents that can potentially improve the performance of fibrinogen-based hemostatic bandages, besides natural ones such as thrombin and other blood coagulation factors. Very recently, the use of propyl gallate and other gallate derivatives has been disclosed to increase the performance of fibrinogen-based hemostatic dressings with hemostatic dressing backings made, among other things, of collagen. U.S. Pat. No. 6,891,077 (2005) to S. W. Rothwell, et al., is an example disclosing this use. Propyl gallate is used in the food industry as an antioxidant additive for oils and fats. The invention offers the capability of incorporating pro-coagulation species, either of natural or synthetic origin, into a fibrinogen hemostatic dressing on a molecular-scale and this is a desirable improvement.

The preferred embodiment of the present invention newly creates the option of occluding propyl gallate and its derivatives within the fibers of the dressing. The Rothwell patent teaches a method of adding a solution of propyl gallate to a bandage, but does not teach using propyl gallate dispersed on a molecular-scale throughout the bandage. The preferred embodiment of the present invention eliminates a cumbersome step of soaking a bandage with aqueous-organic media of non-protein constituents, which in itself is counterproductive because it adds moisture that potentially interferes with formation of a blood clot. Rather, in the preferred embodiment of the present invention, the aqueous-organic media of non-protein constituents is thoroughly mixed part of the solution that is used to make the fibers.

The United States Army has recently used a fibrinogen bandage with a chitosan backing in the battlefield. Besides chitosan, which is a biopolymer derived from the chitin in crustaceans, other polymers such as, but not limited to, polylactic acid, or PLA, and polylactic-co-glycolic acid, or PLGA, may be viewed as good backing materials for a fibrinogen-containing wound dressing. PLA and PLGA degrade in vivo by hydrolysis (esterase activity) into lactic acid and glycolic acid, respectively, which are then incorporated into the tricarboxylic acid metabolic cycle. Besides PLA and PLGA, other bioabsorbable polymers such as, but not limited to, polycaprolactone, and copolymers resulting from combinations thereof, may be used as backing materials for hemostatic dressings. The present invention avoids the use of backing materials or layers and offers the potential to incorporate these polymers directly in or on the fibers of the dressing, creating a high contact surface area promoting rapid blood coagulation.

Fibrinogen has been recently processed into fibers by technique known as electrospinning from 1,1,1,3,3,3-hexafluoroisopropanol solutions. Besides being soluble in water, proteins are often soluble in perfluorinated alcohols such as 1,1,1,3,3,3-hexafluoroisopropanol, and 2,2,2-trifluoropropanol. The acute toxicity of 1,1,1,3,3,3-hexafluoroisopropanol, however, is well documented. Despite the acute toxicity problems, a number of patent applications still describe methods for direct electrospinning of protein solutions in organic solvents for making hemostatic and wound dressings. For example, two of these include United States Patent Application Publication Nos. 2004-0037813 A1 for electrospun collagen and 2004-0229333 A1 for electroprocessed fibrin.

Without the aid of additives that may compromise preservation of the native state of a dissolved protein, or may compromise the intended biological function, electrospinning of aqueous protein solutions, exemplified by PCT application WO/1998/003267 by R. A. Coffee, is generally difficult. Electrospinning a bandage directly on a wound had an initial appeal of making the fibers directly off blood coagulation proteins, avoiding a fibrous backing. However, practical problems in using this approach in situations involving arterial bleeding are that it is time consuming and requires a level of skill not often present. For direct application by electrospinning of aqueous protein solutions to wounds, two additional problems became evident: this electrospinning approach uses a lot more protein than by just coating biocompatible polymer fibers, such as those made from polylactic acid; and, electrospinning of proteins in fluorinated hydrocarbons is cell-toxic if even a trace fluorinated hydrocarbon remains in the fibers.

Electrospinning is used in an embodiment of present invention to create the fibers. This is optionally followed by a drying step to ensure that the solvent is completely gone. The fibers are then coated with one or more blood coagulation proteins. The coating is made from an aqueous solution of the protein to form a molecular-scale coating on fibers of the dressing. This is optionally followed by removal of water from the coating, and optionally a subsequent electrostatic deposition of other proteins of the clotting cascade from dry powders or from aqueous and mixed aqueous-organic media at sub-zero degrees Celsius. This methodology avoids problems with electrospinning poorly biocompatible additives, avoids the unnecessary use of expensive proteins and avoids toxicity altogether. Additionally, the present invention does not make a dressing or bandage when needed at the emergency situation. Rather it is suited only for making the dressing in a manufacturing facility, packaging it, and shipping it for later use.

Accordingly, there is a need for a fibrous hemostatic dressing that improves utilization of blood clotting species via dispersing these species within the fibers of the dressing, or onto the surface of fibers as coatings with thickness comparable in size to the average diameter of the fibers. Thus, the method of the invention delivers a fibrous dressing wherein the individual fibers are coated with blood clotting species that will maximally expose, on first contact with blood, the blood clotting species. The dressing, to with a bandage, would speedily supply active ingredients to the wound in quantities that are not available in the blood coming out of the wound to seal the wound quickly. A dressing made in accordance with the invention does not change the chemistry of the clotting process, but rather delivers blood clotting species at a much higher rate than current dressings. The high surface area of contact of the actives with blood from the wound is what drives a fast clot formation process, while avoiding the use of a large mass of expensive coagulation proteins. In addition, optional biological clot-aiding constituents would improve the natural clotting process by making platelets aggregate at the wound.

DISCLOSURE OF INVENTION

Technical Problem

Arterial wounds are one of the chief causes of death in the battlefield. To avoid death by exsanguination from an arterial wound, an efficient blood clot must be formed at the wound site in a timeframe of generally seconds to a several minutes. Effective hemostatic wound dressings to treat arterial wounds have been traditionally based on a two component system of fibrinogen and thrombin. Fibrinogen is the blood protein that yields the fibrin protein scaffold in a blood clot, with the aid of other clotting agents, such as thrombin. This two component system may consist of a layered dressing, double-syringe applicators, spray systems, or reliance on mixing these components at the injury site to form a fibrin coagulum.

Present dressings are costly and wasteful of blood clotting proteins. The most costly constituents of a hemostatic dressing based on blood clotting cascade proteins are the proteins themselves. By way of example, purification of about 5.0 liters of human plasma normally yields a few grams of fibrinogen, and quantities of thrombin and factor XIIIa, two other important proteins in the blood coagulation cascade, are well below one gram.

Using fibrinogen in layered or other type bandages where macroscopic domains of fibrinogen are present has been a problem in the past because it may prematurely form fibrin before use on a wound. The other two component systems waste the blood clotting proteins in a spray, or form preparations having water-like fluidity which renders them difficult to handle and administer, or have thickening agents that inhibit formation of a robust fibrin coagulum.

The biologically active ingredients of hemostatic dressings for arterial bleeding are usually purified from human plasma, but may also be obtained from transgenic techniques, or from animals. The fibrinogen is often lyophilized onto the material that serves as the hemostatic dressing backing. Efforts to increase fibrinogen content in a hemostatic dressing to deliver better hemorrhage control, deliver dressings with poor mechanical properties, are fragile and not pliable enough to adapt to the varieties of wound sites.

Technical Solution

The present invention solves these problems by depositing a molecular-scale fibrinogen coating on the individual fibers of a bioabsorbable collection of fibers from solutions, and then depositing thrombin or other proteins from their dry powders, or using other methods, such that premature fibrin formation is avoided.

The present invention serves an urgent need for more efficient hemostatic dressings that induce clotting using a minimum of blood coagulation proteins, thereby having the potential to enable use of the invention in both the civilian and military sectors of the population.

The present invention enables a large fibrinogen area of exposure to blood per unit weight of fibrinogen in a dressing.

The present invention creates a dressing with fibers having good mechanical properties causing the dressing to be pliable and adaptable to the any variety of wound site.

The present invention enables use of propyl gallate, its derivatives, and other abiological clot-aiding chemicals by dispersing these chemicals within, or at the surface of the fibers comprising the dressing.

Advantageous Effects

The dressing of the present invention enables efficient utilization of blood clotting species present in arterial blood when the blood clotting ingredients in the dressing contact blood in a hemorrhaging wound, and, unlike much of the prior art, is particularly suited to arterial wounds that tend to bleed profusely.

DESCRIPTION OF DRAWINGS

The drawings, which illustrate several embodiments of the present invention, include reference numbers that are used consistently throughout.

FIG. 1 is a flow diagram of the steps in an embodiment of the invention.

FIG. 2 is a flow diagram of the steps in an alternative embodiment of the invention.

BEST MODE

Figure 3:
FIG. 3 is a confocal fluorescence microscopy photograph of the fibers in a dressing according to one embodiment of the invention.

While this invention is susceptible of embodiments in many different forms, there are shown in the drawings and will herein be described in detail, preferred embodiments of the invention with the understanding that the present disclosure is to be considered as an exemplification of the principles of the invention and is not intended to limit the broad aspect of the invention to the embodiments illustrated.

Embodiments of the invention described herein produce a hemostatic dressing that is bioabsorbable and fibrous with a molecular-scale coating on the fibers, which upon first contact with blood, exposes a significantly greater area per unit weight of blood coagulation protein or proteins to blood from an arterial wound than is possible with current dressings. Using any of these processes results in a pliable, bioabsorbable hemostatic dressing of fibers, each such preferably fiber having a molecular-scale coating that promotes blood clotting when applied to a wound. Using the processes described herein, the individual fibers are not compressed into a paper-like product, but the individual fibers for most embodiments remain accessible to coagulating blood in a contact area above about 3 square meters per gram of coagulation protein.

An embodiment of the method of the invention has 4 steps to produce a dressing with individually coated fibers. However, it is not a requirement that each and every fiber comprising the dressing have a molecular-scale coating of fibrinogen or other blood coagulation protein. Rather, it is sufficient for adequate and economical utilization of the blood coagulation protein that a substantial fraction of the fibers have such a coating. Also, the order of the steps of the invention described herein is not intended to limit the invention to the particular order of steps described. The order of the method steps described may be varied from that described herein. Any order that achieves the same end result dressing is within the scope of the invention.

What follows, in general, describes a process wherein fibers are first created by electrospinning from a solution. This is optionally followed by a drying step to ensure that solvent is completely gone. The fibers are then coated with one or more blood coagulation proteins from a solution. The coating is made from an aqueous solution of the protein to form a molecular-scale coating on fibers of the dressing. This is optionally followed by removal of water from the coating, that is drying the coating, and optionally a subsequent electrostatic deposition of other proteins of the clotting cascade from dry powders or from aqueous and mixed aqueous-organic media at sub-zero degrees Celsius.

A first embodiment of the method of the invention includes (a) a step of dissolving in an organic solvent one or more soluble bioabsorbable polymers and organic or aqueous-organic media of non-protein constituents to create a homogeneous mixture; (b) a step of forming fibers from the homogenous mixture; and (c) a step for adding to the fibers a molecular-scale first coating of one or more proteins of blood clotting species that minimally react with each other.

An alternative preferred embodiment includes a step for adding a second coating of one or more proteins of blood clotting species to the fibers that minimally react with each other and that, together with the one or more proteins of blood clotting species in the molecular-scale first coating, induce blood coagulation in the presence of blood.

The term 'hemostatic' refers to an ability to reduce or stop blood loss from surgical or traumatic wounds by promoting blood clot formation.

The term 'bioabsorbable' refers to the ability of a tissue-compatible material to degrade in the body after implantation into nontoxic products which are eliminated from the body or metabolized.

The term 'fibrous' refers to a composition, which comprises fibers from natural or synthetic materials, that is not compressed into a paper-like fabric or textile material. The preferred diameter of any fiber is the range of ten nanometers to fifty microns.

The bioabsorbable fibrous dressing may optionally have blood clotting species within a fiber and, must have at least one blood coagulation protein dispersed as a coating on the surface of the fibers in a thickness comparable in size to the average diameter of the fibers.

FIG. 1 shows the steps in the first embodiment. A first step (11) is dissolving in an organic solvent one or more soluble bioabsorbable polymers and organic or aqueous-organic media of non-protein constituents to create a homogeneous mixture.

This first step (11) of the first embodiment is a fiber precursor. The fiber precursor is a solution of one or more soluble biopolymers dissolved in an organic solvent or solvent blend that is fairly benign from a biocompatibility standpoint. Typical solvents are ethyl acetate and acetone. Aqueous-alcohol blends or aqueous-alcohol-ethyl acetate blends may also work acceptably well as an organic solvent.

Preferred soluble bioabsorbable polymers are polylactic acid, polylactic glycolic acid, chitosan, chitin, polycaprolactone, poly ethylene oxide, poly ethylene glycol, modified and unmodified polysaccharides, modified and unmodified synthetic polyaminoacids, proteins, poly beta-hydroxybutyric acid), poly beta-hydroxyvaleric acid, polydioxanone, polyphosphazene, poly ethylene terephthalate, poly tartronic acid, poly malic acid, and combinations thereof. Random and block copolymers resulting from the polymers listed in the preceding sentence may also be used. Other therapeutic agents that do not adversely affect the hemostatic function of the dressing may also be included.

Preferred non-protein constituents are chemicals that aid in blood clotting and clot stabilization and include calcium salts, propyl gallate and other gallic acid derivatives, epsilon aminocaproic acid, tranexamic acid, and p-aminomethyl benzoic acid. Propyl gallate and its chemical derivatives are considered to be blood platelet aggregation agents.

Calcium ions can be an important constituent for promoting blood-clotting, and their incorporation in the homogenous mixture is desirable. Divalent calcium cations, calcium ethoxide, calcium 2-ethylhexanoate, and calcium stearate may be dissolved as a constituent of the organic or aqueous organic media. Concentrations of calcium cations may be used up to the saturation value of the organic soluble calcium chemical in the aqueous organic media.

A homogenous mixture is required to ensure that the components of the mixture are molecularly dispersed therein and are consequently uniformly integrated within the fibers produced from the mixture. As a result, no such component will be selectively concentrated in a region of any fiber.

The second step (12) of the first embodiment is forming fibers from the homogenous mixture, that is, the fiber precursor solution. Typically, the fiber precursor solution is electrospun, where most or all of the solvent evaporates during processing. A random fibrous mat of biocompatible polymers is obtained.

FIG. 3 shows the confocal fluorescence microscopy photograph of the fibers (31) in a hemostatic dressing made via electrostatic processing of polylactic acid fibers, which have been coated with fibrinogen. The fibers were fabricated from a solution of 10 wt % polylactic acid in acetone, and the electrostatic processing method was not based on formation of electrified menisci from orifices delivering the fiber fluid precursor. The fibers were then coated with human fibrinogen labeled with a fluorescent dye using an aqueous solution with fibrinogen concentration of 0.65 mM (0.22 mg/mL), and a dye to protein ratio of 18.5. The final weight percentage content of fibrinogen in the coated fibers was 1.4.

The ethyl acetate or any other solvent used to dissolve any biopolymer may contain clot-aiding abiological clotting species, such as propyl gallate and organic calcium salts. If it does contain such abiological clotting species, then the resulting fibrous mat is composed of biopolymeric fibers that have these clot-aiding species dispersed molecularly in their bulk. Optionally, these abiological clot-aiding chemicals may be added as a coating instead of being added to the fiber precursor solution. Propyl gallate and its derivatives are powerful blood platelet aggregators, which is advantageous in thickening blood while forming a clot.

The fibers are preferably with a diameter between ten nanometers to fifty microns made by processes generally known in the art, such as electrostatic spinning, electrostatic processing using methods not based on flow of fiber fluid precursors through orifices, polymer melts, melt blowing, and other fiber drawing mechanical processes, preferably forming fiber whose average diameter falls in the ten-nanometer to fifty-micron range.

The resulting fibers are essentially in the form of a fibrous mat. The fibers are then optionally dried, for example under vacuum or in a low temperature oven, to make sure the solvent is evaporated as completely as practicable. While optional, drying is a good practice because proteins tend to become spoiled or '"denatured' if they remain in contact with organic solvents.

The third step (13) of the first embodiment is adding to the fibers a molecular-scale first coating of one or more proteins of blood clotting species that minimally react with each other. This coating is at a molecular scale in that the molecules of any protein are predominantly uniformly dispersed along the surface of a fiber. Each protein included in the coating must minimally react with each other so as not to compromise the biological or blood clotting function of the dressing.

Proteins of blood clotting species are coagulation-inducing proteins found in blood, or more specifically blood plasma. When a dressing of the present invention is applied to a wound, the proteins of blood clotting species in the fiber coating and the abiological clot-aiding species added to the fibers complement and supplement the coagulation-inducing proteins naturally present in blood released from a wound. These species in the dressing interact chemically in the aqueous environment of the blood to rapidly promote formation of a clot. Blood plasma components called coagulation factors respond in a complex cascade to form fibrin strands. In an arterial wound, the rate-limiting factors for forming a strong clot within seconds to a few minutes is availability of proteins from the clotting cascade, especially fibrinogen and thrombin, in sufficient amounts.

The protein or proteins of blood clotting species for the molecular-scale first coating are typically obtained from purification and fractionation of human plasma, or it may be obtained from animals, transgenic animals or via recombinant, genetic engineering methods. A preferred protein of such blood clotting species is fibrinogen. Human plasma fibrinogen almost invariably is molecularly associated with another blood clotting cascade, namely factor XIII, so a coating of human-derived fibrinogen is typically accompanied by other blood clotting species.

Other proteins of blood clotting species that may be used singly, or in combination only if the combination will not compromise the biological functionality of any protein constituent in the mixture when applied to a wound, are: thrombin, prothrombin, von Willebrand factor, factor XIII, fibronectin, fibrin, aprotinin, antiplasmin, alpha-2 macroglobulin, plasminogen, alpha-1-antitrypsin, and plasmin activator inhibitors, such as but not limited to, PAI-1 or PAI-2. Thrombin catalyzes the conversion of fibrinogen into fibrin in the presence of moisture, which is essentially the blood clot scaffold. So these two proteins may not be used together in the homogenous mixture used for the fiber coating, unless their aqueous solutions are handled at temperatures below zero degrees Celsius, as discussed below in an alternative embodiment. Other proteins that adversely react when mixed together may not be combined in the homogeneous mixture.

The molecular-scale coating molecular-scale coating is achieved by placing the fibrous mat in contact with an aqueous solution of the blood coagulation-inducing protein. Removal of water leads to deposition of a coating of protein over the fibers. The thickness of the coating is a function of the concentration of the coagulation-inducing protein in the aqueous solution. Removal of water may be accomplished by methods known in the art, such as by evaporation under vacuum or partial evacuation, by passing dry air or other gases through, or by the wet hemostatic dressing precursor, by freeze-drying, or by any other method that does not compromise the biological function of the coagulation-inducing protein or proteins.

In the preferred embodiment, this molecular-scale coating is achieved by placing the fibrous mat in contact with an aqueous solution of fibrinogen of adequate concentration so as to coat the fibers with a molecular-scale coating of fibrinogen.

Control of the average thickness of any protein coating deposited onto the fibers is achieved by controlling the concentration of the protein or proteins in the aqueous solution, and the mass ratio of the aqueous solution to fibers.

In alternative preferred embodiment number one, a fourth step is appended to the steps of the first embodiment, namely, a step for adding to the fibers a coating of one or more proteins of blood clotting species that minimally react with each other and that, together with the one or more proteins of blood clotting species in the fibers, induce blood coagulation in the presence of blood. In this embodiment, this step would preferably coat the fibers with thrombin. Unlike the molecular-scale first coating, this second coating may not be performed from an aqueous solution. Thrombin does not react with fibrinogen per se, but it is the powerful biological catalyst such that very little thrombin is needed for it to perform the catalysis. A typical ratio of thrombin to fibrinogen is about 1:100. Thrombin, in the presence of water, cuts fibrinogen into molecular pieces, called fibrinopeptides, and then rearranges them into fibrin, the basic clot scaffold. For an effective dressing, this process of forming fibrin must take place primarily when applied to a wound.

The group of proteins added to the fibers in the second coating is selected from the same group as the proteins of blood clotting species in the molecular-scale first coating and typically would be a complementary protein for inducing blood coagulation.

For example, if fibrinogen were selected as a single protein of blood clotting species added in the molecular-scale first coating, then a complementary coagulation-inducing protein for the second coating would be thrombin. Alternatively if thrombin were selected as a single protein of blood clotting species added in the molecular-scale first coating, then a complementary protein of coagulation-inducing protein would be fibrinogen. Such combinations are well known in the art.

Other coagulation-inducing proteins may be used singly or in combination if such use promotes coagulation when the dressing is applied to a wound. A combination of proteins should be used in a coating only when the combined proteins would not compromise the coagulation-inducing function of the individual proteins in the dressing or in blood from a wound.

Embodiments of the invention employ two alternative procedures to apply the second coating. Thrombin is used as the example to simplify the description.

The first procedure is to load dry thrombin powder into a metallic cup or plate, bias the cup or plate electrically relative to the fibrinogen-loaded fibrous mat, and disperse the dry thrombin powder onto the mat. This procedure will deposit thrombin in particles, which are primarily above about one micron in diameter.

The second procedure is to dissolve thrombin in water or water-glycerol blends. Glycerol, in small amounts, is one of the few organic chemicals that does not significantly denature such proteins. The resulting solution is then electrosprayed onto the fibrinogen-coated fibers. This is done so that most, if not all, of the water or water-glycerol solvent evaporates before it reaches the fibrinogen-coated fibers. Such evaporation is important to avoid formation of fibrin as explained above. The second procedure is not preferred because of the added need to ensure that the thrombin electrospray deposits thrombin, and minimal water, on the fibrinogen-coated fibers. However, this second procedure deposits much finer thrombin particles on the fibers than is accomplished with procedure 1, such that the coating is closer to a preferred molecular-scale thrombin coating.

MODE FOR INVENTION

A second embodiment of the method of the invention is a variation of the first embodiment in that it eliminates the molecular-scale first coating, changes the fiber precursor to include in the list of additives to the homogeneous mixture one or more proteins of blood clotting species that minimally react with each other, and adds another step, namely a step for adding to the fibers a coating of one or more proteins of blood clotting species that minimally react with each other and that, together with the one or more proteins of blood clotting species in the fibers, induce blood coagulation in the presence of blood.

FIG. 2 illustrates the steps in the second embodiment. A first step (21) is dissolving in an organic solvent one or more soluble bioabsorbable polymers, one or more proteins of blood clotting species that minimally react with each other, and organic or aqueous-organic media of non-protein constituents to create a homogeneous mixture. The fiber precursor solution, therefore, includes protein of blood clotting species. The second embodiment thus includes in the homogeneous mixture any proteins that would otherwise have been applied as a coating in the third step (13) of the first embodiment. The molecular-scale first coating step (13) of the first embodiment is, therefore, eliminated in favor of including the protein within the homogeneous mixture that is used to form the fibers. The same named proteins for the first embodiment are used in this step and are subject to the same restriction that if more than one such protein is used that they minimally react with each other so as not to compromise the biological or blood clotting function of the dressing.

The next step (12) in the second embodiment is the same as in the first embodiment.

The third step (21) is adding to the fibers a coating of one or more proteins of blood clotting species that minimally react with each other and that, together with the one or more proteins of blood clotting species in the fibers, induce blood coagulation in the presence of blood. This step adds the step described above for the alternative preferred embodiment number one. The same coating procedures described above for alternative preferred embodiment number one are used for this coating.

In alternatives of this second embodiment, the fibers contain, or as described above are coated with, calcium ions or bioactive agents that promote wound healing and blood clotting, and treatment of wounds, and prevent infection. Such bioactive agents include, are but not limited to polypeptide growth factors, non-steroidal anti-inflammatory agents, antibiotics, and cytostatics. The concentration of the additional components will vary depending on the desired objective.

Dressings can be created with some fibers individually coated in accordance with the method of this invention and combined with other fibers individually coated with other proteins or medicaments to improve the performance of the finished hemostatic dressing. For example, a first group of fibers with fibrinogen and thrombin can be combined with a second group of fibers where the second group fibers have a coating of calcium ions, or simply a group of fibers can contain fibrinogen, thrombin, calcium ions, or other hemostatic proteins, and medicaments.

In yet other alternative embodiments, the steps after forming the fibers are replaced with a step of soaking the fibers in a subcooled, typically below zero degrees Celsius and preferably about minus 4 degrees Celsius, aqueous solution of fibrinogen, thrombin and stabilizing salts which prevent freezing of the solution. The coating is achieved by soaking the fibers in the solution, in which at that subcooled temperature, thrombin will not significantly cleave fibrinogen and repolymerize it into fibrin. The soaked fibers are then freeze-dried to remove the water without raising the temperature. Once dry, the fibrinogen/thrombin molecular-scale coated fibers are then brought to room temperature for packaging. Using a subcooled solution, produces a molecular-scale coating of the fibers with highly dispersed patches of fibrinogen and thrombin, and some regions on the fibers where the two proteins are tangled up together.

The disclosure herein is to be considered as an exemplification of the principles of the invention and is not intended to limit the broad aspect of the invention to the embodiments illustrated or described. Thus, the scope of the invention is determined by the appended claims and their legal equivalents rather than by the examples given.

INDUSTRIAL APPLICABILITY

The invention has applicability to the medical treatment industries.

The invention claimed is:
1. A method of making a pliable, bioabsorbable hemostatic dressing comprising; the steps of:
dissolving in an organic solvent one or more soluble bioabsorbable polymers and organic or aqueous-organic media of non-protein constituents to create a homogeneous mixture;
forming fibers from the homogeneous mixture;
soaking the fibers in an aqueous solution subcooled to below zero degrees Celsius, the solution comprising fibrinogen, thrombin and stabilizing salts, said aqueous subcooled solution prevented from freezing by the stabilizing salts;
freeze-drying the soaked fibers to remove water from the aqueous solution and form a coating without raising the temperature of the aqueous solution; and then
raising the temperature of the fibers to room temperature for packaging.

* * * * *